(12) United States Patent
Cabiri et al.

(10) Patent No.: US 8,876,730 B2
(45) Date of Patent: Nov. 4, 2014

(54) DIAGNOSTIC OR TREATMENT TOOL FOR COLONOSCOPY

(75) Inventors: Oz Cabiri, Macabim (IL); Benad Goldwasser, Tel Aviv (IL)

(73) Assignee: G. I. View Ltd., Ramat Gan (IL)

( * ) Notice: Subject to any disclaimer, the term of this patent is extended or adjusted under 35 U.S.C. 154(b) by 569 days.

(21) Appl. No.: 12/501,554

(22) Filed: Jul. 13, 2009

(65) Prior Publication Data

US 2009/0275857 A1 Nov. 5, 2009

Related U.S. Application Data

(63) Continuation of application No. PCT/IL2008/000076, filed on Jan. 17, 2008.

(60) Provisional application No. 60/881,036, filed on Jan. 17, 2007.

(51) Int. Cl.
| | |
|---|---|
| A61B 10/00 | (2006.01) |
| A61B 5/00 | (2006.01) |
| A61B 1/273 | (2006.01) |
| A61B 1/005 | (2006.01) |
| A61B 1/018 | (2006.01) |
| A61B 1/00 | (2006.01) |
| A61M 25/01 | (2006.01) |
| A61M 25/10 | (2013.01) |
| A61B 17/00 | (2006.01) |
| A61B 17/29 | (2006.01) |

(52) U.S. Cl.
CPC .............. *A61B 1/018* (2013.01); *A61B 1/2736* (2013.01); *A61B 2017/003* (2013.01); *A61B 1/0051* (2013.01); *A61B 2017/2927* (2013.01); *A61B 2017/0034* (2013.01); *A61B 1/00082* (2013.01); *A61M 25/0122* (2013.01); *A61M 25/1002* (2013.01)

USPC ........................... 600/562; 600/561; 600/564

(58) Field of Classification Search
USPC ................... 600/562, 564, 585, 593
See application file for complete search history.

(56) References Cited

U.S. PATENT DOCUMENTS

| 3,895,637 A | 7/1975 | Choy |
|---|---|---|
| 4,012,126 A | 3/1977 | Rosendahl et al. |

(Continued)

FOREIGN PATENT DOCUMENTS

| DE | 3630660 | 3/1988 |
|---|---|---|
| EP | 1586275 A2 | 10/2005 |

(Continued)

OTHER PUBLICATIONS

Supplementary European Search Report from PCT/IL2008/000076, mailed Nov. 5, 2010.

(Continued)

*Primary Examiner* — Adam Eiseman

(57) ABSTRACT

Apparatus (20) is provided for use in a gastrointestinal tract (40) of a patient, including an inflatable device (22) configured to be moved through the gastrointestinal tract (40) to a treatment site in response to a difference between fluid pressure proximal to the inflatable device (22) and fluid pressure distal to the inflatable device (22). An optical system (24) coupled to the inflatable device (22) configured to image the gastrointestinal tract (40). A working channel (32) coupled to the inflatable device (22) and shaped to define a channel lumen therein to provide access from outside of the patient to the treatment site. A tool (34) configured to be passed through the channel lumen and to emerge from a distal end of the working channel (32). The tool (34) comprises a tool steering mechanism (44) to facilitate steering of the tool (34) from outside of the patient. Other embodiments are also described.

9 Claims, 2 Drawing Sheets

(56) References Cited

U.S. PATENT DOCUMENTS

| | | | |
|---|---|---|---|
| 4,040,413 A | 8/1977 | Ohshiro | |
| 4,148,307 A | 4/1979 | Utsugi | |
| 4,176,662 A | 12/1979 | Frazer | |
| 4,224,929 A | 9/1980 | Furihata | |
| 4,403,985 A | 9/1983 | Boretos | |
| 4,647,761 A | 3/1987 | Cojan et al. | |
| 4,690,131 A | 9/1987 | Lyddy, Jr. et al. | |
| 4,714,075 A | 12/1987 | Krauter et al. | |
| 4,976,524 A | 12/1990 | Chiba | |
| 5,259,364 A | 11/1993 | Bob et al. | |
| 5,337,732 A | 8/1994 | Grundfest et al. | |
| 5,473,474 A | 12/1995 | Powell | |
| 5,502,592 A | 3/1996 | Jamieson | |
| 5,662,587 A | 9/1997 | Grundfest et al. | |
| 5,739,852 A | 4/1998 | Richardson et al. | |
| 5,882,108 A | 3/1999 | Fraizer | |
| 5,906,591 A | 5/1999 | Dario et al. | |
| 5,920,376 A | 7/1999 | Bruckstein et al. | |
| 6,007,482 A | 12/1999 | Madni et al. | |
| 6,028,719 A | 2/2000 | Beckstead et al. | |
| 6,115,193 A | 9/2000 | Shu | |
| 6,157,018 A | 12/2000 | Ishiguro et al. | |
| 6,222,683 B1 | 4/2001 | Hoogland et al. | |
| 6,296,608 B1 | 10/2001 | Daniels et al. | |
| 6,304,285 B1 | 10/2001 | Geng | |
| 6,333,826 B1 | 12/2001 | Charles | |
| 6,341,044 B1 | 1/2002 | Driscoll, Jr. et al. | |
| 6,356,296 B1 | 3/2002 | Driscoll, Jr. et al. | |
| 6,373,642 B1 | 4/2002 | Wallerstein et al. | |
| 6,375,366 B1 | 4/2002 | Kato et al. | |
| 6,388,820 B1 | 5/2002 | Wallerstein et al. | |
| 6,424,377 B1 | 7/2002 | Driscoll, Jr. et al. | |
| 6,449,103 B1 | 9/2002 | Charles | |
| 6,459,451 B2 | 10/2002 | Driscoll, Jr. et al. | |
| 6,485,409 B1 | 11/2002 | Voloshin et al. | |
| 6,493,032 B1 | 12/2002 | Wallerstein et al. | |
| 6,500,167 B1 * | 12/2002 | Webster, Jr. | 604/528 |
| 6,503,192 B1 | 1/2003 | Ouchi | |
| 6,597,520 B2 | 7/2003 | Wallerstein et al. | |
| 6,611,282 B1 | 8/2003 | Trubko et al. | |
| 6,646,818 B2 | 11/2003 | Doi | |
| 6,702,735 B2 | 3/2004 | Kelly | |
| 6,704,148 B2 | 3/2004 | Kumata | |
| 2002/0012059 A1 | 1/2002 | Wallerstein et al. | |
| 2002/0107478 A1 | 8/2002 | Wendlandt | |
| 2002/0109772 A1 | 8/2002 | Kuriyama et al. | |
| 2002/0109773 A1 | 8/2002 | Kuriyama et al. | |
| 2003/0000526 A1 | 1/2003 | Gobel | |
| 2003/0052324 A1 | 3/2003 | Kimura | |
| 2003/0083547 A1 | 5/2003 | Hamilton et al. | |
| 2003/0105386 A1 | 6/2003 | Voloshin et al. | |
| 2003/0168068 A1 | 9/2003 | Poole et al. | |
| 2003/0191369 A1 | 10/2003 | Arai et al. | |
| 2004/0004836 A1 | 1/2004 | Dubuc | |
| 2004/0249247 A1 | 12/2004 | Iddan | |
| 2005/0038335 A1 | 2/2005 | Gross et al. | |
| 2005/0154355 A1 | 7/2005 | Gross et al. | |
| 2005/0165272 A1 | 7/2005 | Okada et al. | |
| 2005/0197531 A1 | 9/2005 | Cabiri et al. | |
| 2005/0272975 A1 * | 12/2005 | McWeeney et al. | 600/113 |
| 2006/0164733 A1 | 7/2006 | Gal et al. | |
| 2006/0183975 A1 | 8/2006 | Saadat et al. | |
| 2008/0097292 A1 | 4/2008 | Cabiri et al. | |

FOREIGN PATENT DOCUMENTS

| | | |
|---|---|---|
| JP | 5-43114 | 6/1993 |
| JP | 2006-516910 A2 | 7/2006 |
| WO | 01/68540 | 9/2001 |
| WO | 02/059676 | 8/2002 |
| WO | 02/075348 | 9/2002 |
| WO | WO02068035 A1 | 9/2002 |
| WO | 03/026272 | 3/2003 |
| WO | 03/045487 | 6/2003 |
| WO | 03/046830 | 6/2003 |
| WO | 03/054625 | 7/2003 |
| WO | 03/096078 | 11/2003 |
| WO | 2004/008185 | 1/2004 |
| WO | WO2004010858 A2 | 2/2004 |
| WO | WO2004028354 A1 | 4/2004 |
| WO | 2004/042428 | 5/2004 |
| WO | 2004/069057 | 8/2004 |
| WO | WO 2004/064600 | 8/2004 |
| WO | 2005/065044 | 7/2005 |
| WO | 2005/110186 | 11/2005 |

OTHER PUBLICATIONS

International Search Report and Written Opinion, mailed Jun. 18, 2008, from International Application No. PCT/IL2008/000076, filed Jan. 17, 2008.

* cited by examiner

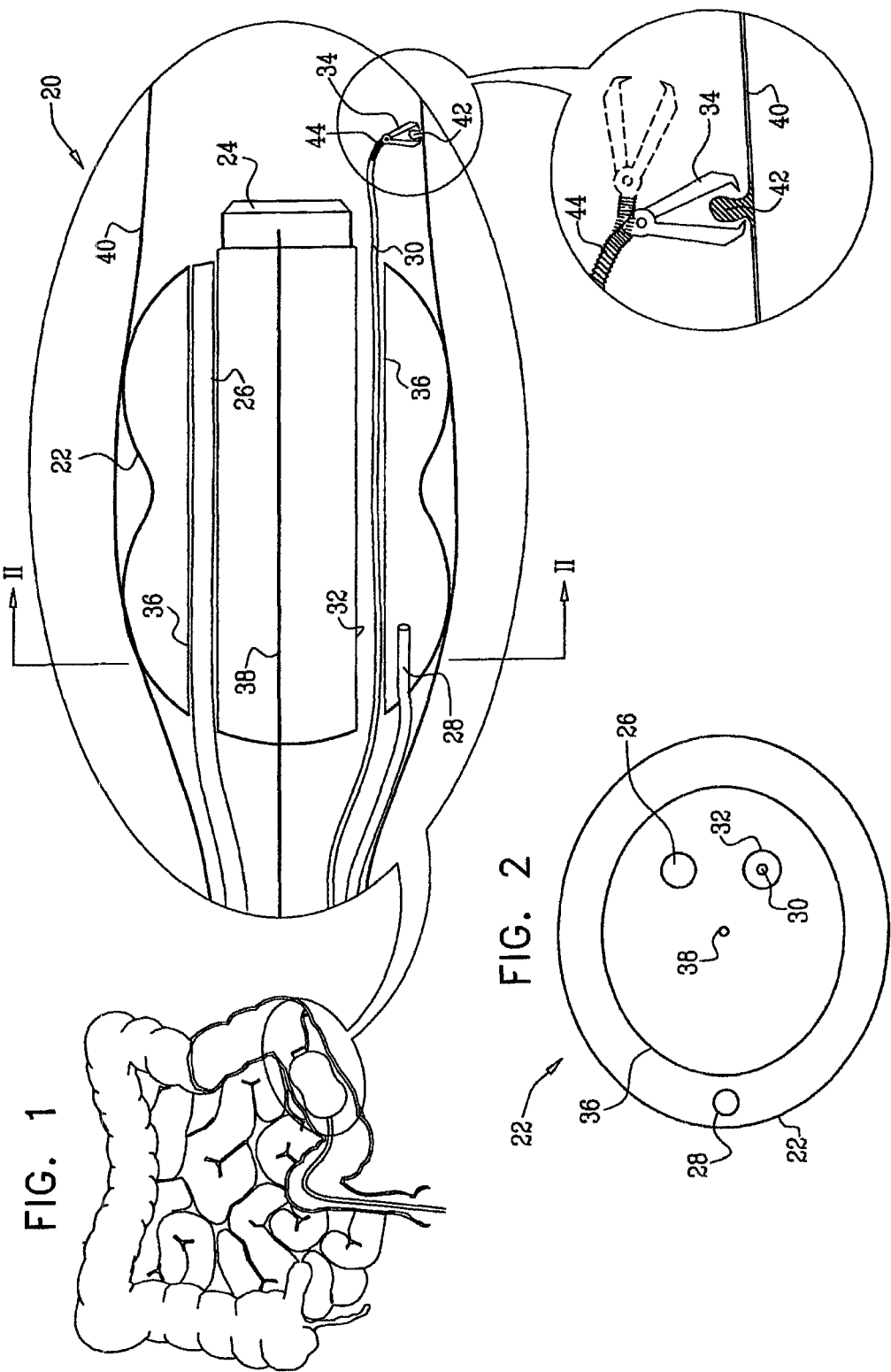

DIAGNOSTIC OR TREATMENT TOOL FOR COLONOSCOPY

RELATED APPLICATIONS

This application is a Continuation of International Application No. PCT/IL2008/000076, filed on Jan. 17, 2008, which claims the benefit under 35 USC 119(e) of U.S. Provisional Application No. 60/881,036, filed on Jan. 17, 2007, both of which are incorporated herein by reference in their entirety.

FIELD OF THE INVENTION

The present invention relates generally to endoscopic tools, and specifically to treatment and diagnostic tools suitable for use in the gastrointestinal (GI) tract.

BACKGROUND OF THE INVENTION

Many imaging and biopsy techniques are known for producing medical images and taking samples from body lumens, such as the gastrointestinal (GI) tract. For example, endoscopy is widely used for observing, photographing tissue, and taking specimens from lesions. In a conventional method of examining a colon, for example, a colonoscope is manually inserted into the colon, and manipulated so as to allow viewing of some or all of the colon. If it is desired to biopsy tissue, a biopsy tool is advanced through a working channel of the colonoscope until it emerges from the distal end of the colonoscope, and appears in the viewing field of an imaging system of the colonoscope. The distal end of the colonoscope is rotated by the physician until the biopsy tool is suitably positioned to allow the tissue to be excised. The excised tissue is then sent for laboratory analysis.

PCT Patent Publication WO 05/065044 to Cabiri et al., which is assigned to the assignee of the present patent application and incorporated herein by reference, describes apparatus for use with a biologically-compatible-fluid pressure source, the apparatus including an elongate carrier, adapted to be inserted through a proximal opening of a body lumen, and a piston head coupled to a distal portion of the carrier. The piston head is adapted to form a pressure seal with a wall of the lumen after the carrier has been inserted into the lumen. The piston head is advanced distally through the body lumen in response to pressure from the fluid pressure source. The apparatus is configured to facilitate distal advancement of the piston head by facilitating passage of fluid out of the lumen from a site within the lumen distal to the piston head. The apparatus additionally includes an optical system, coupled to the carrier in a vicinity of the distal portion, the optical system having distal and proximal ends. The optical system includes an image sensor, positioned at the proximal end of the optical system; an optical member having distal and proximal ends, and shaped so as to define a lateral surface, at least a distal portion of which is curved, configured to provide omnidirectional lateral viewing; and a convex mirror, coupled to the distal end of the optical member, wherein the optical member and the mirror have respective rotational shapes about a common rotation axis. In an embodiment, a sufficient net pressure force results in distal movement of the piston head along with the elongate carrier and a tool. The tool may comprise an imaging device, a biopsy device, or other apparatus to be used in the body lumen.

U.S. Pat. No. 6,296,608 to Daniels et al., which is incorporated herein by reference, describes a catheter for diagnosing and performing an interventional procedure on tissue. The catheter has an elongated catheter shaft, and optical fibers, extending through the catheter shaft. The optical fibers transmit light to tissue located at a distal end of the catheter and convey light back from the tissue for analysis by a spectroscopic diagnosis system to determine whether an interventional procedure should be performed on the tissue. An interventional device is located at the distal end of the catheter for engaging tissue diagnosed by the spectroscopic diagnosis system in order to perform the interventional procedure on the tissue. An assembly for imaging and performing an interventional procedure on tissue has an endoscope in combination with an endoscopically insertable catheter. The endoscopically insertable catheter has an ultrasound imaging device for imaging a tissue structure located at a distal end of the endoscope so as to enable the depth of penetration of the tissue structure to be displayed. The endoscopically insertable catheter has an endoscopically insertable interventional device for engaging the tissue structure imaged by the ultrasound imaging device. The following references may be of interest, and are incorporated herein by reference:

PCT WO 01/68540 to Friend
PCT WO 02/059676 to Gal
PCT WO 02/075348 to Gal
PCT WO 03/026272 to Gal
PCT WO 03/045487 to Gobel
PCT WO 03/046830 to Gal
PCT WO 03/054625 to Gal
PCT WO 03/096078 to Gal
PCT WO 04/008185 to Gal
PCT WO 04/042428 to Gal
PCT WO 04/069057 to Gobel
US 2002/0012059 to Wallerstein
US 2002/0107478 to Wendlandt
US 2002/0109772 to Kuriyama
US 2002/0109773 to Kuriyama
US 2003/0000526 to Gobel
US 2003/0052324 to Kimura
US 2003/0083547 to Hamilton
US 2003/0105386 to Voloshin
US 2003/0168068 to Poole
US 2003/0191369 to Arai
US 2004/0004836 to Dubuc
US 2004/0249247 to Iddan
US 2006/0164733 to Gal
U.S. Pat. No. 4,012,126 to Rosendahl
U.S. Pat. No. 4,040,413 to Ohshiro
U.S. Pat. No. 4,148,307 to Utsugi
U.S. Pat. No. 4,176,662 to Frazer
U.S. Pat. No. 4,403,985 to Boretos
U.S. Pat. No. 4,647,761 to Cojan
U.S. Pat. No. 4,690,131 to Lyddy, Jr.
U.S. Pat. No. 4,714,075 to Krauter
U.S. Pat. No. 4,976,524 to Chiba
U.S. Pat. No. 5,259,364 to Bob
U.S. Pat. No. 5,337,732 to Grundfest
U.S. Pat. No. 5,473,474 to Powell
U.S. Pat. No. 5,502,592 to Jamieson
U.S. Pat. No. 5,662,587 to Grundfest
U.S. Pat. No. 5,739,852 to Richardson
U.S. Pat. No. 5,882,108 to Fraizer
U.S. Pat. No. 5,906,591 to Dario
U.S. Pat. No. 5,920,376 to Bruckstein
U.S. Pat. No. 6,007,482 to Madni
U.S. Pat. No. 6,028,719 to Beckstead
U.S. Pat. No. 6,115,193 to Shu
U.S. Pat. No. 6,157,018 to Ishiguro
U.S. Pat. No. 6,222,683 to Hoogland U.S. Pat. No. 6,304,285 to Geng
U.S. Pat. No. 6,333,826 to Charles
U.S. Pat. No. 6,341,044 to Driscoll, Jr.
U.S. Pat. No. 6,356,296 to Driscoll, Jr.
U.S. Pat. No. 6,373,642 to Wallerstein
U.S. Pat. No. 6,375,366 to Kato
U.S. Pat. No. 6,388,820 to Wallerstein
U.S. Pat. No. 6,424,377 to Driscoll, Jr.
U.S. Pat. No. 6,449,103 to Charles
U.S. Pat. No. 6,459,451 to Driscoll, Jr.
U.S. Pat. No. 6,485,409 to Voloshin
U.S. Pat. No. 6,493,032 to Wallerstein
U.S. Pat. No. 6,503,192 to Ouchi
U.S. Pat. No. 6,597,520 to Wallerstein
U.S. Pat. No. 6,611,282 to Trubko
U.S. Pat. No. 6,646,818 to Doi
U.S. Pat. No. 6,702,735 to Kelly
U.S. Pat. No. 6,704,148 to Kumata

SUMMARY OF THE INVENTION

In some embodiments of the present invention, apparatus is provided comprising an endoscope for use in a gastrointestinal tract of a patient. The apparatus comprises an inflatable device, which is configured to be moved by fluid pressure through the gastrointestinal tract towards a treatment site. An optical system is coupled to the inflatable device, and images the gastrointestinal tract, in order to enable a physician to determine if a region being imaged by the optical system includes a target tissue that should be biopsied, examined, and/or treated. If so, a suitable tool is advanced through a working channel that is coupled to the inflatable device. The tool is configured to be passed through a channel lumen of the working channel, and to emerge from a distal end of the working channel. The tool comprises a tool steering mechanism to facilitate steering of the tool from outside of the patient.

The tool steering mechanism is typically controllable using techniques known in the art for transvascular or other intrabody steering of a tool or other longitudinal member, and may be controlled manually or robotically. Once the tool has exited the working channel, the steering mechanism of the tool typically enables the tool to be steered towards the target tissue even in the absence of any steering that may be provided by other portions of the apparatus (e.g., steering that may tilt the working channel towards the target tissue). For some applications, the working channel is not tilted at all to bring the tool nearer to the target tissue.

In an embodiment, the apparatus comprises a guide other than an endoscope. For example, the guide may comprise a laparoscope or a guide for examination, biopsy, or treatment of an air passage of the patient. Regardless of the form of the guide, the guide typically (but not necessarily) comprises an omnidirectional optical system. Use of a tool with a tool steering mechanism, as described herein, is particularly suitable for use with a guide having an omnidirectional optical system, because the omnidirectional optical system can remain generally stationary, providing full omnidirectional imaging, while the tool with the tool steering mechanism moves independently, in order to interact with tissue anywhere in the field of view of the omnidirectional optical system, in a manner desired by the physician.

There is therefore provided, in accordance with an embodiment of the invention, apparatus for use in a gastrointestinal tract of a patient, including:

an inflatable device, configured to be moved through the gastrointestinal tract to a treatment site, in response to a difference between fluid pressure proximal to the inflatable device and fluid pressure distal to the inflatable device;

an optical system, coupled to the inflatable device, and configured to image the gastrointestinal tract;

a working channel, coupled to the inflatable device, and shaped to define a channel lumen therein to provide access from outside of the patient to the treatment site; and a tool, configured to be passed through the channel lumen and to emerge from a distal end of the working channel, the tool including a tool steering mechanism to facilitate steering of the tool from outside of the patient.

In an embodiment, the tool includes a biopsy tool.
In an embodiment, the tool includes a treatment tool.
There is also provided, in accordance with an embodiment of the invention, apparatus for use with a tool that includes a tool steering mechanism to facilitate steering of the tool from outside of a patient, the apparatus configured for use in a gastrointestinal tract of the patient, including:

an inflatable device, configured to be moved through the gastrointestinal tract to a treatment site, in response to a difference between fluid pressure proximal to the inflatable device and fluid pressure distal to the inflatable device;

an optical system, coupled to the inflatable device, and configured to image the gastrointestinal tract; and a working channel, coupled to the inflatable device, and shaped to define a channel lumen for passage of the tool therethrough.

There is additionally provided, in accordance with an embodiment of the invention, apparatus for use with a tool that includes a tool steering mechanism to facilitate steering of the tool from outside of a patient, the apparatus configured for use in a gastrointestinal tract of the patient, including:

a device, configured to be moved through the gastrointestinal tract to a treatment site; and a working channel, coupled to the device, and shaped to define a channel lumen for passage of the tool therethrough.

There is yet additionally provided, in accordance with an embodiment of the invention, a method for controlling an endoscope that includes a working channel, including:

placing the endoscope in a lumen of a patient;
advancing an endoscopic tool through the working channel; and
utilizing a steering capacity of the endoscopic tool to control the endoscope.

In an embodiment, controlling the endoscope includes tilting a distal tip of the endoscope by utilizing the steering capacity of the tool.

In an embodiment, utilizing the steering capacity of the tool includes determining that distal motion of the endoscope is at least partially blocked, and restoring the distal motion of the endoscope by utilizing the steering capacity of the tool.

There is still additionally provided, in accordance with an embodiment of the invention, a method for advancing an endoscope that includes a working channel, including:

placing the endoscope in a lumen of a patient;
advancing an endoscopic tool through the working channel; and
utilizing a stiffness of the endoscopic tool to facilitate advancement of the endoscope.

In an embodiment, the endoscope includes an inflatable device, and wherein placing the endoscope in the lumen includes advancing the endoscope through the lumen by applying pressure to an external surface of the inflatable device.

In an embodiment, utilizing the stiffness of the tool includes determining that distal motion of the endoscope is at least partially blocked, and restoring the distal motion of the endoscope by pushing the tool.

There is also provided, in accordance with an embodiment of the invention, a method for using an endoscopic tool passed through an endoscope that includes a working channel, including:

placing the endoscope in a gastrointestinal tract of a patient;

advancing the endoscopic tool through the working channel and out of a distal end of the endoscope; and steering the endoscopic tool without steering the distal end of the endoscope.

There is further provided, in accordance with an embodiment of the invention, a method for using a tool passed through a guide that includes a working channel and an omnidirectional optical system, including:

placing the guide in a body of a patient;

advancing the tool through the working channel and out of a distal end of the guide; and steering the tool independently of any steering of the distal end of the guide, while viewing the tool with the omnidirectional optical system.

In an embodiment, the guide includes a laparoscope, and placing the guide includes placing the laparoscope in the body of the patient.

In an embodiment, the guide includes a guide configured for operation in an air passage of the patient, and placing the guide includes placing the guide in the air passage.

In an embodiment, the guide includes an endoscope, and placing the guide includes placing the endoscope in the body of the patient.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a schematic illustration of apparatus for performing a biopsy, in accordance with an embodiment of the present invention;

FIG. 2 is a cross-sectional illustration of the apparatus of FIG. 1, in accordance with an embodiment of the present invention;

DETAILED DESCRIPTION OF THE PREFERRED EMBODIMENTS

Figure 3:
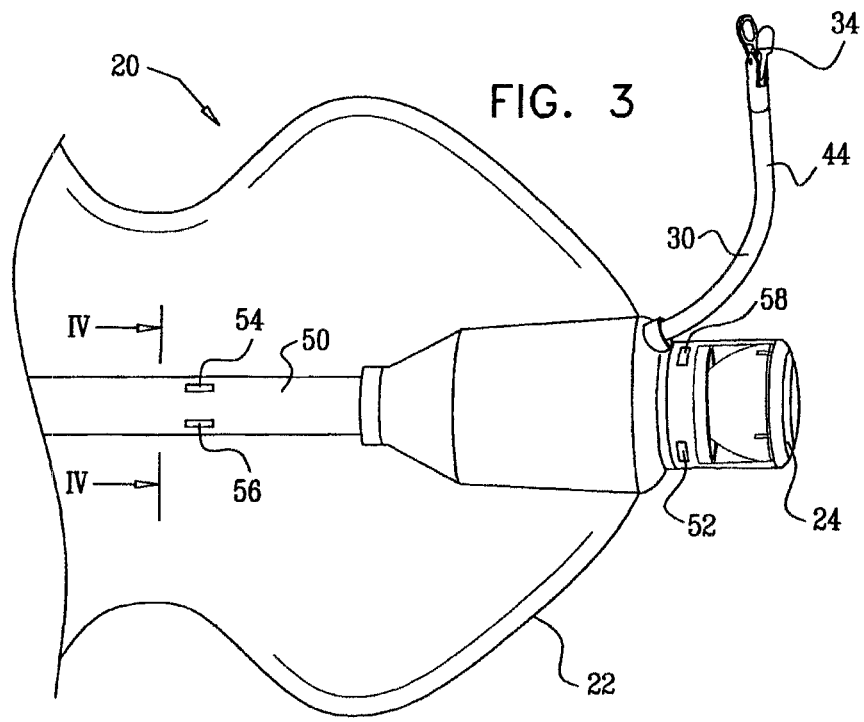
FIG. 3 is an illustration of the apparatus of FIG. 1, in accordance with an embodiment of the present invention.

Reference is made to FIGS. 1 and 2, which are a schematic illustration and a cross-sectional illustration, respectively, of apparatus 20 for performing a biopsy, in accordance with an embodiment of the present invention. A biopsy is shown by way of illustration and not limitation, and the scope of the present invention includes apparatus for performing other procedures, such as treatment or diagnostic procedures. Apparatus 20 is inserted into and advanced through a gastrointestinal tract 40 of a patient, typically using techniques described in PCT Patent Publication WO 05/065044 to Cabiri et al. Apparatus 20 comprises an inflatable device 22, which is configured to be moved through the gastrointestinal tract to a treatment site, in response to a difference between fluid pressure proximal to the inflatable device and fluid pressure distal to the inflatable device. The apparatus may thus be advanced distally (to the right in FIG. 1) by application of a fluid pressure proximal to the inflatable device that is greater than the pressure distal to the inflatable device. Similarly, the apparatus may be moved proximally by application of a fluid pressure distal to the inflatable device that is greater than the pressure proximal to the device. Such distal fluid pressure is typically conveyed via a distal-communication lumen 26. Alternatively or additionally, apparatus 20 is moved proximally through the gastrointestinal tract by being pulled by an operator of the apparatus.

An optical system 24, typically an omnidirectional optical system, is coupled to inflatable device 22 and images gastrointestinal tract 40, in order to enable a physician to determine if a region being imaged by the optical system includes a target tissue 42 that should be biopsied, examined, and/or treated. If so, a tool 34 (e.g., a therapeutic tool or a diagnostic tool such as a biopsy tool) is advanced through a working channel 32 that is coupled to the inflatable device. For some applications, inflatable device 22 is toroidal, and working channel 32 passes through the hole defined by the toroidal shape of the inflatable device. (An outermost extent of the hole is indicated by dashed line 36 in FIG. 1.) Tool 34 is passed through a channel lumen of working channel 32, and emerges from a distal end of the working channel.

Tool 34 comprises a tool steering mechanism 44 to facilitate steering of the tool from outside of the patient. The exploded view in FIG. 1 shows a previous position of tool 34 in dashed lines, and a current position of the tool (around the target tissue) in solid lines. Thus, as shown, the tool is typically able to be steered by steering mechanism 44 independently of any motion of working channel 32. Typically, inflatable device 22 is stationary after tool 34 has been advanced out of the distal end of working channel 32. If appropriate, the inflatable device is advanced or withdrawn slightly within gastrointestinal tract 20, to facilitate a procedure performed by the tool (e.g., a biopsy or treatment). This motion, however, typically does not involve tilting of the inflatable device so as to better position the tool with respect to target tissue 42. (It is noted that although some embodiments of the present invention are described with respect to the inflatable device not being tilted during a procedure, the scope of the present invention includes such tilting, if appropriate for a given procedure.)

Tool steering mechanism 44 itself typically comprises control wires within a sheath 30, or other apparatus known in the art for remote steering of an intra-lumen tool.

Typically, the toroidal shape of inflatable device 22 allows various tubes and wires to be in fluid or electrical communication with control and analysis apparatus outside of the patient's body. For example, a distal-communication lumen 26 may allow pressure to be vented from the region distal to the inflatable device to outside of the patient's body. Alternatively or additionally, an intra-balloon lumen 28 allows the pressure within the inflatable device to be regulated.

FIG. 3 is an illustration of apparatus 20, in accordance with an embodiment of the present invention. It is noted that steering mechanism 44 of tool 34 is typically able to direct the tool to substantially any site of the gastrointestinal tract within view of optical system 24. Thus, for example, the tool can typically be advanced and retracted longitudinally, bent using wires within the tool, and rotated by rotating the body of the tool within the working channel.

Figure 4:
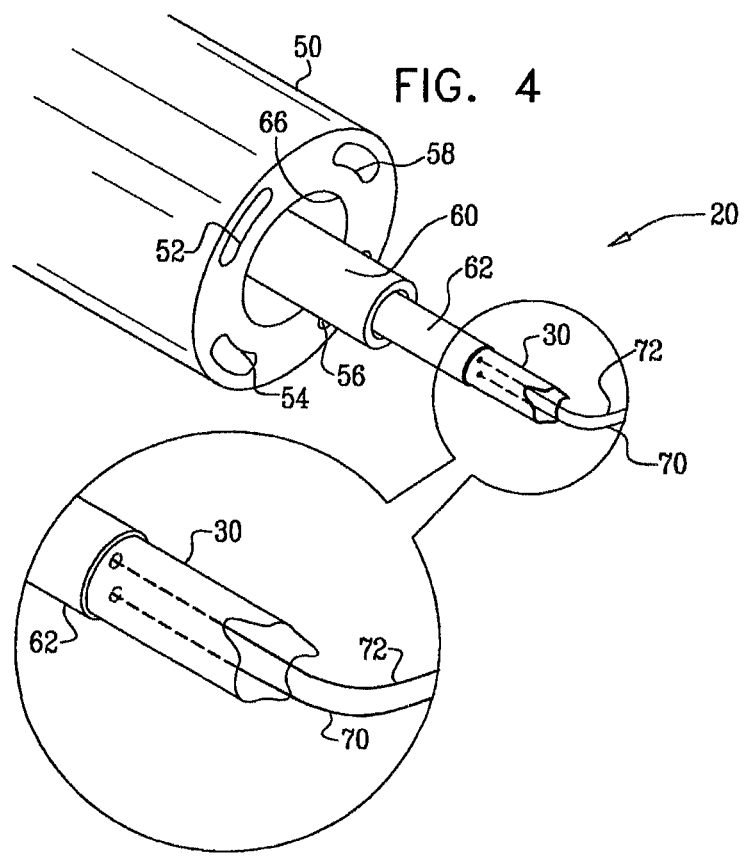
FIG. 4 is a schematic illustration of a supply cable for the apparatus of FIG. 1, in accordance with an embodiment of the present invention.

FIG. 4 is a schematic illustration of apparatus 20, in accordance with an embodiment of the present invention. A multi-lumen supply cable 50 provides lumens 52, 54, 56, and 58, respectively, for:

(1) supplying water,
(2) controlling various inflatable device ("balloon") pressures,
(3) sensing various inflatable device ("balloon") pressures, and
(4) sensing gastrointestinal tract pressures (e.g., sensing pressure distal to apparatus 20).

Examples of suitable apparatus for moving an instrument through the gastrointestinal tract are shown in the figure; other examples are described in the above-referenced WO 05/065044 to Cabiri et al. Typically, supply cable 50 is disposed within working channel 32. As shown in FIG. 3, at least a portion of supply cable 50 is typically disposed longitudinally within inflatable device 22. The portion disposed within inflatable device 22 is shaped to define openings for respective distal ends of lumens 54 and 56 such that lumens 54 and 56 are in fluid communication with the inside of inflatable device 22. The openings in supply cable 50 for lumens 54 and 56 within inflatable device 22 facilitate the respective controlling and sensing of various inflatable device pressures (it being understood that one opening is also suitable for both functions, for some applications).

Openings are provided at the distal end of apparatus 20 for lumens 52 and 58. These openings facilitate, respectively, (1) supplying of water to gastrointestinal tract 40, and (2) the sensing of gastrointestinal tract pressures distal to apparatus 20.

Reference is now made to FIGS. 3 and 4, which are schematic illustrations of intraluminal apparatus, in accordance with respective embodiments of the present invention. A primary lumen 66 of supply cable 50 is configured for passage therethrough of a cable 60 (such as an electrical cable) (FIG. 4). Typically, cable 60 comprises a hollow tube shaped to define a lumen for passage therethrough of a tool tube 62 for tool 34 (not shown in FIG. 4 for clarity of illustration). As shown in FIG. 3, a functional working tool 34 is disposed at a distal end of working tool sheath 30. Working tool sheath 30 is typically flexible and configured for sliding advancement though tool tube 62. Typically, a wire 70 is disposed within working tool sheath 30 and facilitates bending and/or steering of sheath 30, and thereby tool 34. Additionally, a wire 72 is disposed within working tool sheath 30 and facilitates the operation of tool 34. Wires 70 and 72 extend through the entire apparatus 20 such that respective proximal ends of wires 70 and 72 are disposed outside the body of the patient. Respective distal ends of wires 70 and 72 are therefore controllable by the operating physician from outside the body of the patient.

Wires 70 and 72 are shown as being disposed in separate lumens within sheath 30 by way of illustration and not limitation. Alternatively, wires 70 and 72 are disposed within the same lumen within sheath 30.

Typically, working tool sheath 30 is configured for sliding advancement through tool tube 62. As such, various working tools may be advanced through tool tube 62. For example, following the use of tool 34, the operating physician may pull on a proximal end of sheath 30 in order to extract tool 34 from apparatus 20. Subsequently, the physician may advance a different tool through tool tube 62.

Typically, but not necessarily, the procedure is performed in the patient's colon. Alternatively, the procedure is performed in another site of the gastrointestinal tract.

Some embodiments of the present invention have been described herein and shown in the figures with respect to a biopsy tool. This is by way of illustration and not limitation, and the scope of the present invention includes the use of tools other than biopsy tools, such as diagnostic and treatment tools. For example, tool 34 may comprise a biopsy tool (e.g., as shown in FIGS. 1 and 3), such as a polypectomy snare or any other tissue retrieval mechanism; a therapeutic or diagnostic needle; a treatment tool such as for performing ablation, endoscopic tattooing (e.g., to mark a polyp), manipulating mucosal tissue, endoscopic resection, or another treatment or minimally-invasive surgical procedure; a drug administration tool; an endoscopic cytology tool; or an imaging tool such as a spectral imaging tool. In an embodiment of the present invention, a tool like a conventional tool that has no steering capacity (such as a commercially-available tool in this list of tools) is supplemented by the addition of one or more steering wires to the conventional tool. For some applications, such an enhanced tool is used in combination with an endoscope such as is shown in the figures, or in the above-cited Cabiri PCT publication.

In an embodiment, the steering capacity provided by tool 34 is used to control an endoscope. The endoscope controlled by the tool may be a conventional endoscope (e.g., a conventional colonoscope) or, alternatively, an endoscope such as is shown in the figures, or in the above-cited Cabiri PCT publication. In an embodiment, tool 34 tilts a distal tip of the endoscope. For some applications, if it is determined that distal motion of the endoscope is at least partially blocked, the distal motion may be restored by utilizing the steering capacity of the tool (e.g., to maneuver the endoscope).

Alternatively or additionally, the stiffness of tool 34 is used to facilitate advancement of an endoscope (e.g., an endoscope such as is shown in the figures, or in the above-cited Cabiri PCT publication). For example, the stiffness of the tool may be used to restore or support the distal motion of the endoscope by pushing the tool.

It is noted that although apparatus 20 is described in some embodiments as including an inflatable device to provide movement through gastrointestinal tract 40, the scope of the present invention includes the use of (a) a tool having a steering mechanism, in combination with (b) a conventional endoscope (e.g., a conventional colonoscope), which is advanced through the gastrointestinal tract by being pushed from outside of the patient's body.

The scope of the present invention includes embodiments described in one or more of the following:

U.S. patent application Ser. No. 10/753,424 to Gross et al., entitled, "Pressure-propelled system for body lumen," filed Jan. 9, 2004;

U.S. patent application Ser. No. 10/838,648 to Gross et al., entitled, "Pressure-propelled system for body lumen," filed May 3, 2004;

U.S. patent application Ser. No. 10/967,922 to Cabiri et al., entitled, "Pressure-propelled system for body lumen," filed Oct. 18, 2004;

PCT Patent Application PCT/IL05/000008 to Cabiri et al., entitled, "Pressure-propelled system for body lumen," filed Jan. 3, 2005;

PCT Patent Application PCT/IL05/000500 to Dotan et al., entitled, "Omnidirectional and forward-looking imaging device," filed May 11, 2005;

U.S. patent application Ser. No. 10/596,971 to Cabiri et al., entitled, "Pressure-propelled system for body lumen," filed Jun. 30, 2006; and U.S. Provisional Patent Application 60/881,036 to Cabiri et al., entitled, "Diagnostic and treatment tool for colonoscopy," filed Jan. 17, 2007.

All of these applications are incorporated herein by reference. Techniques described herein can be practiced in combination with techniques described in one or more of these applications.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Apparatus for use in a gastrointestinal tract of a patient comprising an endoscope, said endoscope, comprising:
    an inflatable device, configured to be moved through the gastrointestinal tract to a treatment site, in response to a difference between fluid pressure proximal to the inflatable device and fluid pressure distal to the inflatable device, such that said apparatus is advanced distally by application of said fluid pressure proximal to said inflatable device;
    an optical system, coupled to the inflatable device, and configured to image the gastrointestinal tract in a certain field of view;
    a working channel being shaped to define a channel lumen therein to provide access from outside of the patient to the treatment site, said working channel passing through a hole in the inflatable device;
    a multi-lumen supply cable at least a portion of which is disposed within the inflatable device in said working channel, said multi lumen supply cable comprising:
        a first lumen of supply cable configured for passage therethrough of an electrical cable;
        and a plurality of additional lumens;
        a cable passing through one of said additional lumens, said cable comprising a hollow tube passing therethrough, the hollow tube having a shape that defines at least one tool lumen for advancement therethrough of a tool comprising a tool steering mechanism configured and operable to direct the tool, being advanced towards a treatment site through said tool lumen, to substantially any site of the gastrointestinal tract within said field of view of said optical system to facilitate steering of the tool from outside of a body of the patient; and
    wherein at least one additional lumen being in fluid communication with the inside of the inflatable device;
    and wherein the additional lumens are configured for at least one of the following: supplying water to said gastrointestinal tract, controlling pressure inside said inflatable device, sensing pressure inside said inflatable device, and sensing gastrointestinal tract pressures distal to said apparatus.

2. The apparatus according to claim 1, wherein said steering mechanism comprises control wires disposed within a tool sheath of the tool, wherein
    said tool sheath is flexible and configured for sliding advancement through the hollow tool, and
    said tool is configured to be advanced and retracted longitudinally, bent, and rotated by rotating a body of the tool within the working channel.

3. The apparatus according to claim 2, wherein said control wires extend through the apparatus and comprise respective proximal and distal ends such that respective proximal end of said wires are disposed outside said body and respective distal ends are controllable from outside of said body.

4. The apparatus according to claim 1, wherein said optical system is configured to provided an omnidirectional imaging.

5. The apparatus according to claim 1, comprises a control unit configured and operable to control the tool steering mechanism while the apparatus remain stationary.

6. The apparatus according to claim 1, wherein said tool has a certain stiffness selected to facilitate advancement of the apparatus, to restore or support distal motion of the apparatus by pushing the tool.

7. The apparatus according to claim 1, wherein said tool comprises an endoscopic tool.

8. The apparatus according to claim 1, wherein the inflatable device is toroidal.

9. The apparatus according to claim 1, wherein the cable is an electrical cable.

* * * * *